US012082840B2

United States Patent
Heavey

(10) Patent No.: US 12,082,840 B2
(45) Date of Patent: *Sep. 10, 2024

(54) SURGICAL INSTRUMENT WITH TIP FOR RESECTION OF TISSUE WITH COMBINED LONGITUDINAL AND TORSIONAL VIBRATION

(71) Applicant: Stryker European Operations Holdings LLC, Kalamazoo, MI (US)

(72) Inventor: Cathal Heavey, Midleton (IE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/328,102

(22) Filed: May 24, 2021

(65) Prior Publication Data

US 2021/0275208 A1 Sep. 9, 2021

Related U.S. Application Data

(63) Continuation of application No. 15/843,740, filed on Dec. 15, 2017, now Pat. No. 11,109,880, which is a
(Continued)

(51) Int. Cl.
*A61B 17/32* (2006.01)
(52) U.S. Cl.
CPC ............... *A61B 17/320068* (2013.01); *A61B 2017/320078* (2017.08); *A61B 2017/320098* (2017.08)
(58) Field of Classification Search
CPC .... A61B 17/320068; A61B 17/320092; A61B 2017/320069; A61B 2017/32007;
(Continued)

(56) References Cited

U.S. PATENT DOCUMENTS

| 473,231 A | 4/1892 | Ieffel |
| 3,609,056 A | 9/1971 | Hougen |

(Continued)

FOREIGN PATENT DOCUMENTS

| AT | E427705 T1 | 4/2009 |
| BR | PI0801330 A2 | 8/2009 |

(Continued)

OTHER PUBLICATIONS

English language abstract and machine-assisted English translation for BRPI 0801330 extracted from Thomson Innovations database on Mar. 7, 2018, 22 pages.
(Continued)

*Primary Examiner* — Kankindi Rwego
(74) *Attorney, Agent, or Firm* — Howard & Howard Attorneys PLLC

(57) ABSTRACT

A surgical instrument configured to be coupled to an ultrasonic oscillation mechanism for resection of tissue under suction. A tip extends from a shaft and includes teeth formed by slots. Each of the teeth includes a distal end, a distal cutting edge, and a side cutting edge. The distal cutting edge and the side cutting edge are configured to slice the tissue with the tip moving in a first direction of combined longitudinal and torsional vibration and pull the tissue with the tip moving in the second direction opposite the first direction. An intersection of an outer edge, the distal cutting edge, and the side cutting edge defines a sharp cutting point at the distal end. A sloped surface defining the slot maintains coupling of the tip with the tissue with suction during resection of the tissue with the distal cutting edge and the side cutting edge.

21 Claims, 8 Drawing Sheets

Related U.S. Application Data continuation of application No. PCT/US2016/037582, filed on Jun. 15, 2016.

(60) Provisional application No. 62/180,656, filed on Jun. 17, 2015.

(58) Field of Classification Search
CPC ....... A61B 2017/320071; A61B 2017/320072; A61B 2017/320073; A61B 2017/320074; A61B 2017/320075; A61B 2017/320077; A61B 2017/320078; A61B 2017/32008; A61B 2017/320082; A61B 2017/320084; A61B 2017/320088; A61B 2017/320089; A61B 2017/32009; A61B 2017/320093; A61B 2017/320094; A61B 2017/320095; A61B 2017/320097; A61B 2017/320098; A61B 17/1624; A61B 17/1695
USPC ........................................................ 606/169
See application file for complete search history.

(56) References Cited

U.S. PATENT DOCUMENTS

| | | | |
|---|---|---|---|
| 3,765,789 A | 10/1973 | Hougen | |
| 3,896,811 A | 7/1975 | Storz | |
| 4,063,557 A | 12/1977 | Wuchinich et al. | |
| 4,265,621 A | 5/1981 | McVey | |
| 4,452,554 A | 6/1984 | Hougen | |
| 4,750,902 A | 6/1988 | Wuchinich et al. | |
| 4,823,793 A | 4/1989 | Angulo et al. | |
| 4,827,911 A | 5/1989 | Broadwin et al. | |
| 4,931,047 A | 6/1990 | Broadwin et al. | |
| 4,949,718 A | 8/1990 | Neuwirth et al. | |
| D313,074 S | 12/1990 | Kijima et al. | |
| 5,015,227 A | 5/1991 | Broadwin et al. | |
| 5,221,282 A | 6/1993 | Wuchinich | |
| D339,419 S | 9/1993 | Hood et al. | |
| 5,366,468 A | 11/1994 | Fucci et al. | |
| 5,456,689 A | 10/1995 | Kresch et al. | |
| 5,830,192 A | 11/1998 | Van Voorhis | |
| 6,068,642 A | 5/2000 | Johnson et al. | |
| 6,162,235 A | 12/2000 | Vaitekunas | |
| 6,497,715 B2 | 12/2002 | Satou | |
| 6,503,263 B2 | 1/2003 | Adams | |
| 6,588,992 B2 | 7/2003 | Rudolph | |
| D478,383 S | 8/2003 | Timm et al. | |
| 6,723,110 B2 | 4/2004 | Timm et al. | |
| 6,902,558 B2 | 6/2005 | Laks | |
| D511,002 S | 10/2005 | Easley | |
| 6,955,680 B2 | 10/2005 | Satou et al. | |
| 7,553,313 B2 | 6/2009 | Bagby | |
| 7,556,459 B2 | 7/2009 | Rompel | |
| 7,658,136 B2 | 2/2010 | Rompel et al. | |
| 7,740,088 B1 | 6/2010 | Bar-Cohen et al. | |
| 8,092,475 B2 | 1/2012 | Cotter et al. | |
| 8,118,823 B2 | 2/2012 | Cotter et al. | |
| 8,142,460 B2 | 3/2012 | Cotter et al. | |
| 8,430,897 B2 | 4/2013 | Novak et al. | |
| 8,531,064 B2 | 9/2013 | Robertson et al. | |
| 8,668,032 B2 | 3/2014 | Langhart | |
| 9,358,017 B2 | 6/2016 | Rad | |
| 9,636,132 B2 | 5/2017 | Nguyen et al. | |
| 11,109,880 B2 * | 9/2021 | Heavey | A61B 17/320068 |
| 2001/0011176 A1 | 8/2001 | Boukhny | |
| 2001/0014805 A1 | 8/2001 | Burbank et al. | |
| 2001/0037106 A1 | 11/2001 | Shadduck | |
| 2002/0020417 A1 | 2/2002 | Nikolchev et al. | |
| 2002/0022835 A1 | 2/2002 | Lee | |
| 2002/0029054 A1 | 3/2002 | Rabiner et al. | |
| 2002/0031745 A1 | 3/2002 | Kumar et al. | |
| 2002/0052617 A1 | 5/2002 | Anis et al. | |
| 2002/0124853 A1 | 9/2002 | Burbank et al. | |
| 2003/0018255 A1 | 1/2003 | Martin et al. | |
| 2003/0158566 A1 | 8/2003 | Brett | |
| 2003/0204199 A1 | 10/2003 | Novak et al. | |
| 2004/0030268 A1 | 2/2004 | Weng et al. | |
| 2004/0243136 A1 | 12/2004 | Gupta et al. | |
| 2005/0105981 A1 | 5/2005 | Byrley et al. | |
| 2006/0178698 A1 | 8/2006 | McIntyre et al. | |
| 2006/0184190 A1 | 8/2006 | Feiler et al. | |
| 2006/0189972 A1 | 8/2006 | Grossman | |
| 2006/0190003 A1 | 8/2006 | Boukhny et al. | |
| 2006/0287658 A1 | 12/2006 | Mujwid et al. | |
| 2007/0006215 A1 | 1/2007 | Epstein et al. | |
| 2007/0055179 A1 | 3/2007 | Deem et al. | |
| 2007/0093791 A1 | 4/2007 | Happonen et al. | |
| 2007/0255267 A1 | 11/2007 | Diederich et al. | |
| 2008/0097467 A1 | 4/2008 | Gruber et al. | |
| 2008/0208231 A1 | 8/2008 | Ota et al. | |
| 2008/0228180 A1 | 9/2008 | Epstein | |
| 2009/0142731 A1 | 6/2009 | Kim | |
| 2009/0187182 A1 | 7/2009 | Epstein et al. | |
| 2009/0221998 A1 | 9/2009 | Epstein et al. | |
| 2009/0312692 A1 | 12/2009 | Cotter et al. | |
| 2010/0121197 A1 | 5/2010 | Ota et al. | |
| 2011/0109880 A1 | 5/2011 | Nummela | |
| 2012/0029353 A1 | 2/2012 | Slayton et al. | |
| 2012/0245575 A1 | 9/2012 | Epstein et al. | |
| 2013/0096587 A1 * | 4/2013 | Smith | A61B 17/320758 606/159 |
| 2013/0096596 A1 | 4/2013 | Schafer | |
| 2013/0103066 A1 | 4/2013 | Rad | |
| 2015/0088181 A1 | 3/2015 | Van Tol et al. | |
| 2015/0105791 A1 | 4/2015 | Truckai | |
| 2018/0103976 A1 | 4/2018 | Heavey | |

FOREIGN PATENT DOCUMENTS

| | | |
|---|---|---|
| CN | 1215317 A | 4/1999 |
| CN | 1935095 A | 3/2007 |
| CN | 101674780 A | 3/2010 |
| CN | 101817102 A | 9/2010 |
| DE | 102011084792 A1 | 4/2013 |
| EP | 2233085 A1 | 9/2010 |
| GB | 1457544 A | 12/1976 |
| GB | 2106018 A | 4/1983 |
| GB | 2160129 A | 12/1985 |
| IT | 1256668 B | 12/1995 |
| JP | S4877488 A | 10/1973 |
| JP | S5215832 B1 | 5/1977 |
| JP | S56172073 U | 12/1981 |
| JP | S5859712 A | 4/1983 |
| JP | S5880116 U | 5/1983 |
| JP | H1043923 A | 2/1998 |
| JP | 2001505800 A | 5/2001 |
| JP | 2001191295 A | 7/2001 |
| JP | 2008119250 A | 5/2008 |
| JP | 2009131634 A | 6/2009 |
| JP | 2011517601 A | 6/2011 |
| JP | 2015507510 A | 3/2015 |
| SU | 936897 A1 | 6/1982 |
| WO | 2006059120 A1 | 6/2006 |
| WO | 2008038307 A1 | 4/2008 |
| WO | 2008118709 A1 | 10/2008 |
| WO | 2009126309 A2 | 10/2009 |
| WO | 2010151619 A2 | 12/2010 |
| WO | 2013056262 A1 | 4/2013 |
| WO | 2013057179 A1 | 4/2013 |
| WO | 2014077920 A1 | 5/2014 |

OTHER PUBLICATIONS

English language abstract and machine-assisted English translation for CN 101817102 extracted from espacenet.com database on May 6, 2020, 7 pages.

English language abstract for CN 1215317 extracted from espacenet.com database on May 6, 2020, 2 pages.

English language abstract for CN 1935095 extracted from espacenet.com database on May 6, 2020, 1 page.

English language abstract for IT 1256668 extracted from espacenet.com database on Mar. 7, 2018, 1 page.

(56) References Cited

OTHER PUBLICATIONS

English language abstract for JP 2001-505800 extracted from espacenet.com database on Sep. 10, 2020, 1 page.
English language abstract for JP 2008-119250 extracted from espacenet.com database on Sep. 10, 2020, 1 page.
English language abstract for JP 2015-507510 extracted from espacenet.com database on Sep. 10, 2020, 1 page.
English language abstract for JPS 58-59712 extracted from espacenet.com database on Sep. 10, 2020, 2 pages.
English language abstract not found for JPS 48-77488; however, see English language equivalent U.S. Pat. No. 3,765,789. Original document extracted from espacenet.com database on Sep. 10, 2020, 13 pages.
English language abstract not found for JPS 52-15832; however, see English language equivalent U.S. Pat. No. 3,609,056. Original document extracted from espacenet.com database on Sep. 10, 2020, 14 pages.
Integra Lifesciences Corporation, "Integra Ultrasonics Cusa Nxt Products Catalogue", 2012, 12 pages.
Integra Neurosciences, "CUSA Sheartip", 2009, 2 pages.
International Search Report for Application No. PCTUS2016/037582 dated Sep. 9, 2016, 7 pages.
Machine-Assisted English translation for JPS 58-80116 extracted from the espacenet.com database on Sep. 10, 2020, 3 pages.
Machine-assisted English translation for SU 936897 extracted from espacenet.com database on Mar. 7, 2018, 8 pages.
Misonix, "Sonastar Ultrasonic Surgical Aspiration System", 2013, 8 pages.
Stryker, "Sonopet Product Catalog", 2013, 20 pages.
English language abstract and machine-assisted English translation for JPH 10-43923 A extracted from espacenet.com database on Aug. 24, 2022, 5 pages.
English language abstract and machine-assisted English translation for JP 2001-191295 A extracted from espacenet.com database on Aug. 24, 2022, 6 pages.
English language abstract for JP 2009-131634 A extracted from espacenet.com database on Aug. 24, 2022, 2 pages.
English language abstract for CN 101674780 A extracted from espacenet.com database on Jan. 29, 2024, 2 pages.
English language abstract for DE 10 2011 084 792 A1 extracted from espacenet.com database on Jan. 29, 2024, 1 page.
English language abstract for WO 2013/057179 A1 extracted from espacenet.com database on Jan. 29, 2024, 1 page.
English language abstract for JP 2011-517601 A extracted from espacenet.com database on Mar. 13, 2024, 1 page.
English language abstract for ATE 427705 T1 extracted from espacenet.com database on Jul. 8, 2024, 2 pages.
English language abstract and machine-assisted English translation for JPS 56-172073 U extracted from espacenet.com database on Jul. 8, 2024, 4 pages.
English language abstract and original Chinese language document of FANG, Ai-ling, "In Vitro Treatment of Tumor: Ultrasonic Scalpel", Tianjin Medical Unicersity of Cancer Institute and Hospital, Jul. 25, 2009, 4 pages.

\* cited by examiner

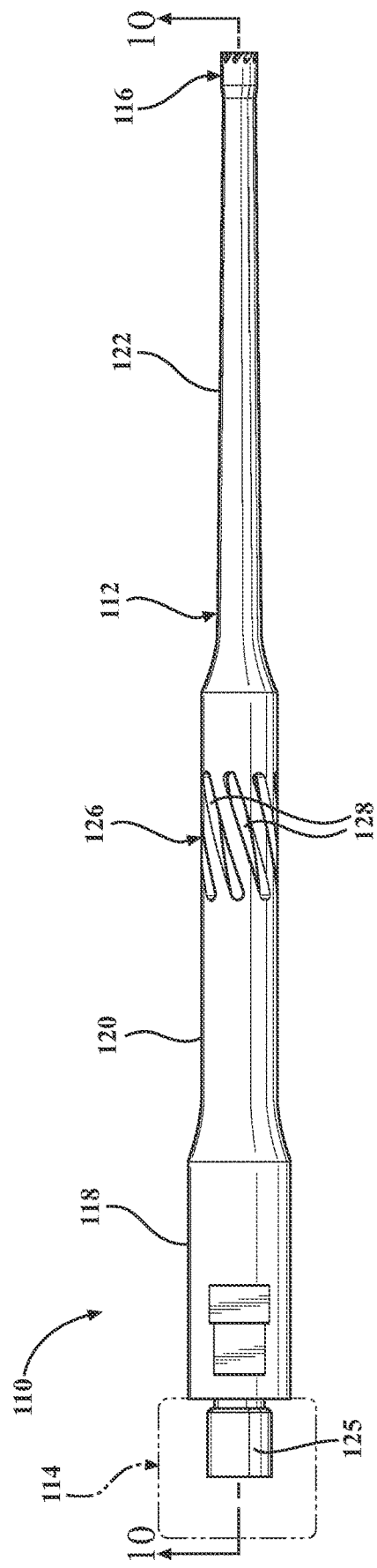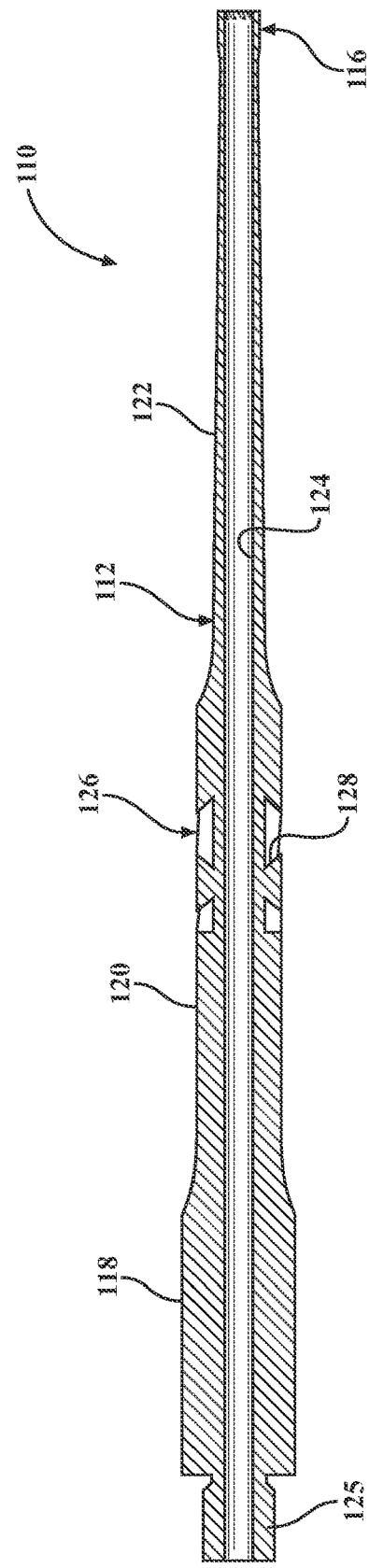

SURGICAL INSTRUMENT WITH TIP FOR RESECTION OF TISSUE WITH COMBINED LONGITUDINAL AND TORSIONAL VIBRATION

CROSS-REFERENCE TO RELATED APPLICATIONS

The present application is a continuation application of copending U.S. application Ser. No. 15/843,740, filed Dec. 15, 2017, which is a continuation of International Application No. PCT/US2016/037582, filed on Jun. 15, 2016, which claims the benefit of U.S. Provisional Patent Application No. 62/180,656, filed Jun. 17, 2015, each of which is hereby incorporated by reference in its entirety.

TECHNICAL FIELD

The present invention relates generally to surgical instruments and, more particularly to, an ultrasonic tip and a surgical instrument with an ultrasonic tip for fibrous tissue removal for use on patients.

BACKGROUND

Medical practitioners have found it useful to use ultrasonic surgical instruments to assist in the performance of certain surgical procedures. An ultrasonic surgical instrument is designed to be applied to a surgical site on a patient. The practitioner positions the ultrasonic surgical instrument at the site on the patient at which the ultrasonic surgical instrument is to perform a medical or surgical procedure. Generally, an ultrasonic surgical instrument includes an ultrasonic handpiece that contains at least one piezoelectric driver. An ultrasonic tip is used in conjunction with the ultrasonic handpiece for removing tissue, specifically fibrous, elastic, tenacious and tough tumor tissue that is difficult to remove with currently available surgical instruments. In at least one type of surgical procedure, surgeons use the ultrasonic surgical instrument to precisely remove tumor tissue.

Known ultrasonic tips typically have a threaded connecting end and a contacting end. The threaded connecting end attaches to the ultrasonic handpiece which provides ultrasonic vibrational motion into the tip and further allows for aspiration through the tip. An ultrasonic tool system typically includes a control console. The control console supplies a drive signal to the ultrasonic handpiece. Upon the application of the drive signal to the driver, the driver cyclically expands and contracts. The expansion/contraction of the driver induces a like movement in the tip and more, particularly, the head of the tip. The energy causes the tip to move, such that the tip is considered to vibrate. The vibrating head of the tip is applied against tissue in order to perform a specific surgical or medical task. For example, some tip heads are applied against hard tissue. One form of hard tissue is bone. When this type of tip head is vibrated, the back and forth vibrations of teeth of the tip, saw, remove, the adjacent hard tissue. Still other tips are designed to ablate and remove soft tissue. Such tips are often designed to induce cavitation in and/or mechanically dissect soft tissue.

For an ultrasonic surgical instrument, sometimes called a handpiece or tool, to efficiently function, a drive signal having the appropriate characteristics should be applied to the tool. If the drive signal does not have the appropriate characteristics, a head of the tip may undergo vibrations of less than optimal amplitude and/or may not vibrate at the maximum amplitude possible. If the handpiece is in either state, the ability of the handpiece to, at a given instant, remove tissue may be appreciably reduced. One way of ensuring an ultrasonic handpiece operates efficiently is to apply a drive signal to the handpiece that is at the resonant frequency of the handpiece. The application of the drive signal at this frequency induces vibrations in the tip that are at a maximum amplitude.

In use, the surgeon or assistant, first installs the tip within a mating end of an acoustic horn of the ultrasonic driver of the ultrasonic handpiece. This is accomplished by screwing the tip into the mating end and applying the proper torque. Once installed, the surgeon may, if desired or necessary for the surgery, place an irrigation sleeve or flue around the tip aft of the contacting end before the operation begins. The irrigation sleeve allows the handpiece to provide irrigation fluid to the surgical site through the ultrasonic handpiece. During the surgical procedure, the surgeon places the contacting end onto or near the tissue or tumor which he or she desires to remove. Once placed, the surgeon then energizes the ultrasonic handpiece and the vacuum aspiration system if desired. The ultrasonic energy transmitted to the contacting end then creates an ultrasonic field relative to the axis of the tip. This field is of such energy that the liquid or tissue surrounding it cavitates and/or breaks down. The tip also resects fibrous tissue. This allows for removal of the material through the interior tube portion of the tip via the vacuum aspiration.

While suitable for some applications, surgeons have found that the fibrous tissue removal rate of currently available ultrasonic tips and devices in not adequate for certain tissues, including some tumors. It has also been found that, with use of standard ultrasonic tips, the fibrous and tough tissue can become tougher, and further impede removal. Overall, the devices that are currently used are inadequate at removing certain fibrous tumors in terms of control of removal and time to remove. Therefore, there is a need in the art to provide a new ultrasonic tip and an ultrasonic surgical instrument having the ultrasonic tip for fibrous tissue removal for use on a patient.

SUMMARY

Accordingly, the present invention provides an ultrasonic tip for a surgical instrument for use on a patient including a head portion adapted to be coupled to a shaft to be applied to a surgical site of a patient, the head portion extending axially along an axial axis to a distal end, the distal end having a cutting edge with a positive rake angle relative to the axial axis for cutting tissue at the surgical site of the patient.

The present invention also provides a surgical instrument for use on a patient including a shaft extending axially between a proximal end and a distal end. The surgical instrument also includes an ultrasonic tip coupled to the distal end of the shaft to be applied to a surgical site of a patient and having a head portion extending axially along an axial axis to a distal end, the distal end of the ultrasonic tip having a cutting edge with a positive rake angle relative to the axial axis for cutting tissue at the surgical site of the patient.

The present invention further provides a method of operating a surgical instrument having an ultrasonic tip including the steps of applying a signal to the surgical instrument and ultrasonically exciting an ultrasonic tip of the surgical instrument, moving the ultrasonic tip into contact with tissue at a surgical site of a patient, the ultrasonic tip having a head portion extending axially along an axial axis to a distal end, the distal end of the ultrasonic tip having a cutting edge with a positive rake angle relative to the axial axis, and cutting fibers in the tissue against the positive rake angle of the cutting edge of the head portion of the ultrasonic tip.

One advantage of the present invention is that a new ultrasonic tip for a surgical instrument is provided for fibrous tissue removal for use on patients. Another advantage of the present invention is that the surgical instrument having the ultrasonic tip allows for the removal of fibrous tissue, primarily fibrous and tough tumor tissue, that is otherwise difficult or not possible to remove safely. Yet another advantage of the present invention is that the surgical instrument having the ultrasonic tip enables controlled removal of fibrous tissue with significantly increased resection rates because the tissue is efficiently cut and resected. Still another advantage of the present invention is that, when the surgical instrument having the ultrasonic tip is applied, the fibrous tissue does not become tougher and therefore harder to resect.

A further advantage of the present invention is that the ultrasonic tip has a distal end utilizing positive rake angle cutting edges to achieve efficient resection of fibrous tissue. Yet a further advantage of the present invention is that the ultrasonic tip has a distal end with outer edges of distal end geometry that enable efficient fiber cutting. Still a further advantage of the present invention is that the ultrasonic tip has a distal end with torsional motion of the distal end or a combined longitudinal and torsional motion that enables greater cutting ability. Yet still a further advantage of the present invention is that the ultrasonic tip has a positive rake angle cutting edge at the inner diameter that causes slicing of the tissue when it is pulled into a central lumen, the size of the resected tissue being no greater than an inner diameter of the tip resulting in reduced chance of clogging of the suction path.

Another advantage of the present invention is that the ultrasonic tip has distal end surfaces that may be orientated on different planes to each other and the sides of the distal portion of the tip may not be perpendicular. Yet another advantage of the present invention is that the ultrasonic tip may be coated with a coating to reduce friction between the tip and the tissue and maintain a sharp cutting edge. Still another advantage of the present invention is that the surgical instrument with an ultrasonic tip allows for faster removal of tumor tissue and therefore a corresponding reduction in surgery time.

Other features and advantages of the present invention will be readily appreciated, as the same becomes better understood, after reading the subsequent description.

BRIEF DESCRIPTION OF THE DRAWINGS

FIG. 9 is an elevational view of the surgical instrument of FIG. 8.

FIG. 10 is a sectional view of the surgical instrument of FIG. 9.

DETAILED DESCRIPTION

Figure 1:
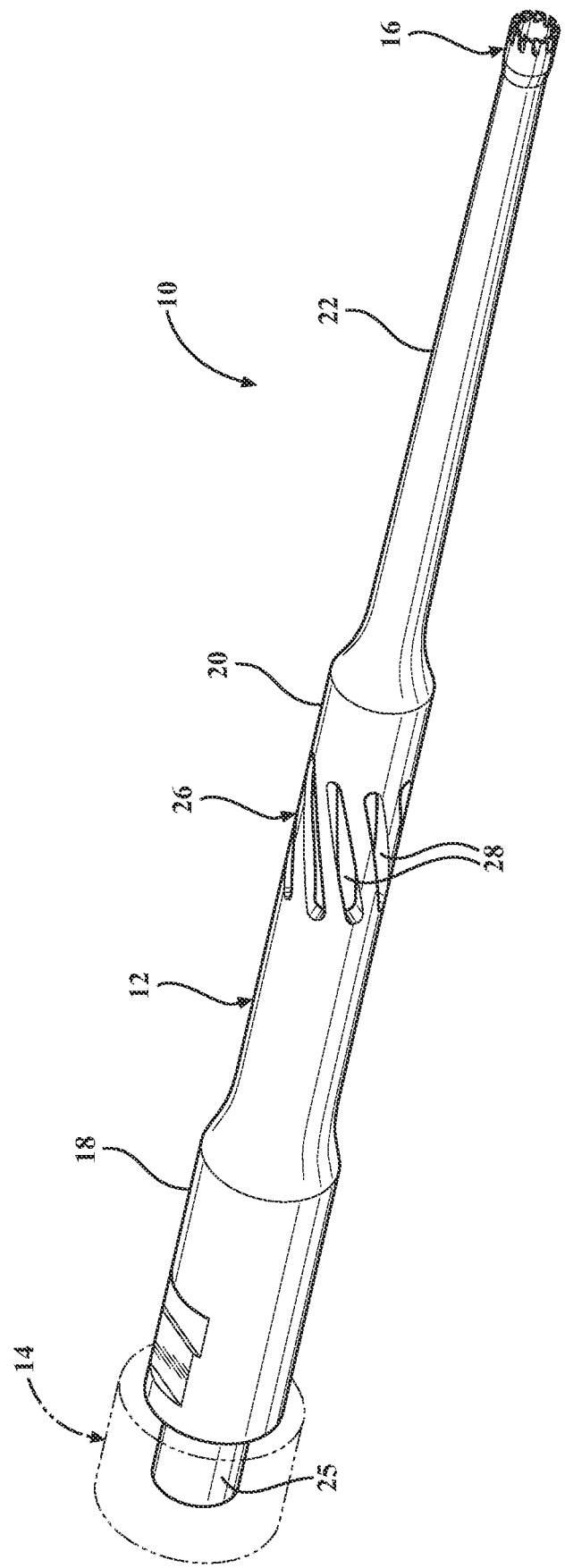
FIG. 1 is a perspective view of one embodiment of a surgical instrument with an ultrasonic tip for fibrous tissue removal, according to the present invention.
Figure 2:
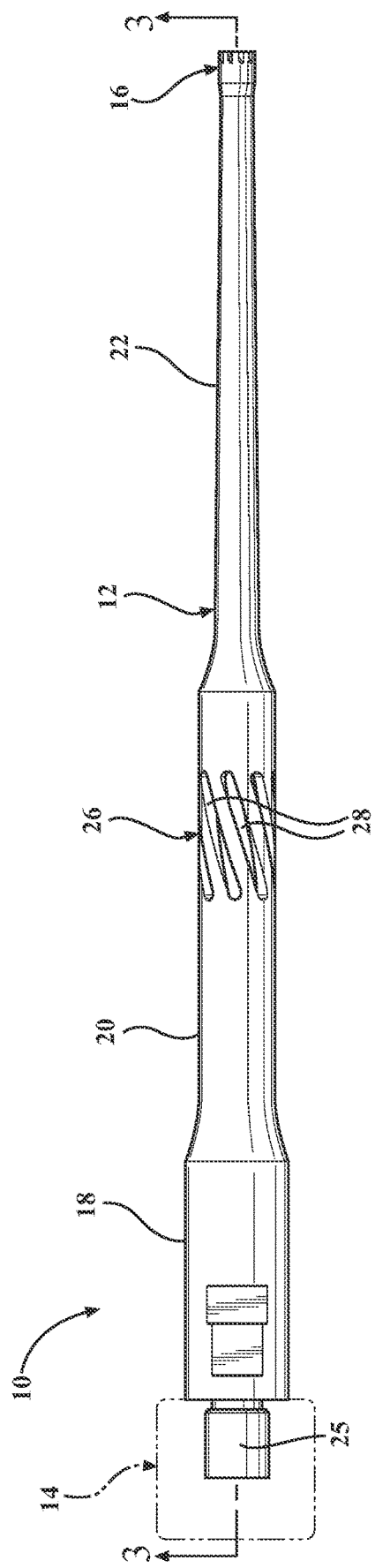
FIG. 2 is an elevational view of the surgical instrument of FIG. 1.
Figure 3:
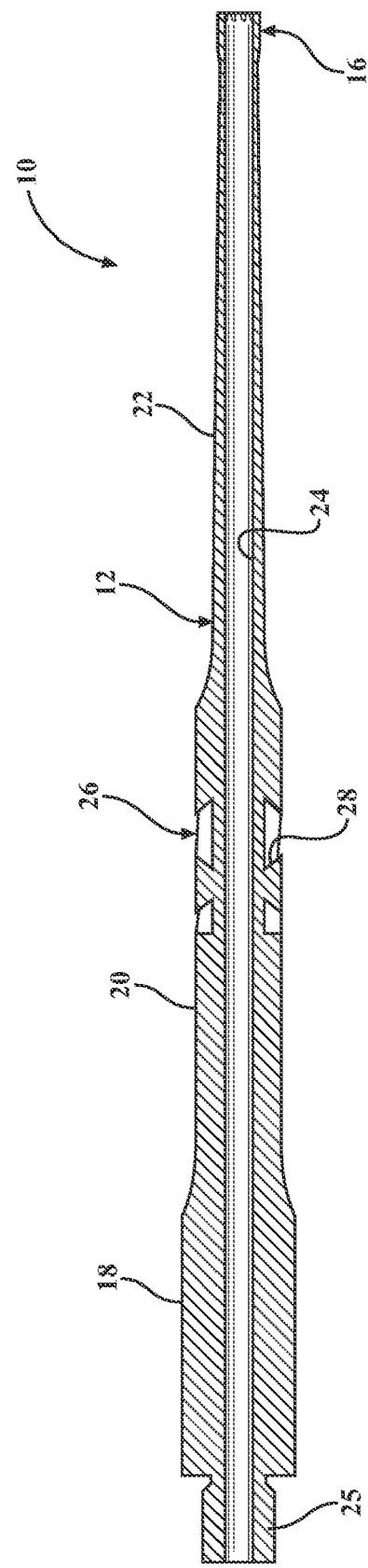
FIG. 3 is a sectional view of the surgical instrument of FIG. 2
Figure 4:
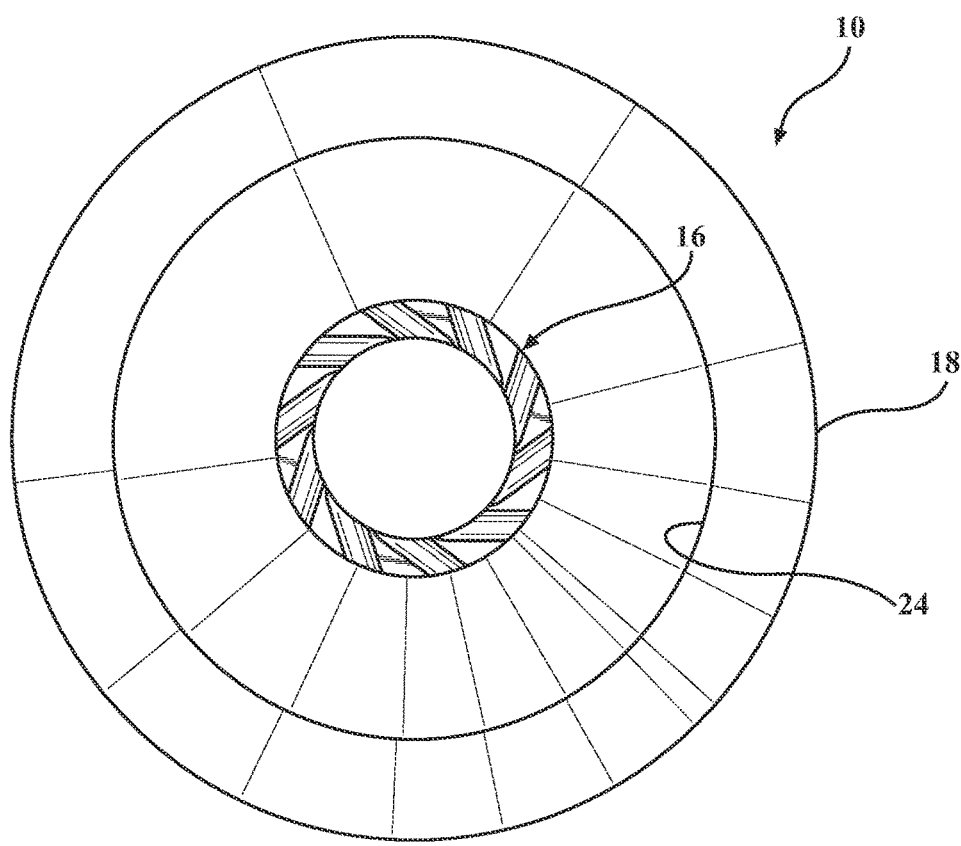
FIG. 4 is a proximal end view of the surgical instrument of FIG. 1.

Referring to FIGS. 1 and 2, one embodiment of a surgical instrument 10, according to the present invention, is shown for use in a medical procedure for a patient (not shown). As illustrated, the surgical instrument 10 includes a horn or shaft, generally indicated at 12, extending between a proximal end and a distal end, an ultrasonic oscillation mechanism 14 at the proximal end, and an ultrasonic tip, according to the present invention and generally indicated at 16, at the distal end for fibrous tissue removal on the patient. The fibrous tissue may include tumor locations on the brain, spinal cord, or other critical anatomy of the patient, including tumor removal in neurosurgery. It should be appreciated that the ultrasonic oscillation mechanism 14 produces ultrasonic wave oscillation for the ultrasonic tip 16. It should also be appreciated that an example of such an ultrasonic oscillation mechanism is disclosed in U.S. Pat. No. 6,955,680 to Satou et al., the disclosure of which is incorporated by reference in its entirety. It should further be appreciated that the surgical instrument 10 may be operated by a user (not shown) such as a surgeon.

Referring to FIGS. 1 through 4, the shaft 12 is a generally hollow cylinder and has a generally circular cross-sectional shape. The shaft 12 extends axially along a central axis from the proximal end to the distal end and has a proximal portion 18, a middle portion 20, and a distal portion 22, respectively. The proximal portion 18 has a diameter greater than a diameter of the middle portion 20 and the middle portion 20 has a diameter greater than a diameter of the distal portion 22. In this embodiment, the distal portion 22 is tapered toward the ultrasonic tip 16. The shaft 12 has a passageway or central lumen 24 extending axially therethrough from the proximal end to the ultrasonic tip 16. The proximal portion 18 has a connecting portion 25 extending axially for connection to the ultrasonic oscillation mechanism 14. It should be appreciated that the ultrasonic oscillation mechanism 14 is connected to the connecting portion 25 of the proximal portion 18 of the shaft 12. It should also be appreciated that the shaft 12 has an external geometry profile that results in a vibrational amplitude gain along a length thereof to the ultrasonic tip 16. It should further be appreciated that the shaft 12 may be linear or arcuate in shape.

The shaft 12 is made of a metal material such as titanium alloy, stainless steel, etc. or a non-metallic material such as a composite, depending on the application. The shaft 12 is integral, unitary, and one-piece. In one embodiment, the shaft 12 and tip 16 may be integral, unitary, and one-piece. In another embodiment, the distal end of the tip 16 may be attached to the shaft 12 by a suitable mechanism such as threads (not shown). It should be appreciated that metals are known in the art regarding high power ultrasonic components. It should also be appreciated that the diameters of the distal portion 22 of the shaft 12 and the ultrasonic tip 16 have a relatively small diameter, for example less than one centimeter (1 cm), so as to work in a small opening of the patient. It should further be appreciated that the shaft 12 and ultrasonic tip 16 may be scaled larger or smaller depending on the application.

The surgical instrument 10 also includes a vibration conversion mechanism, generally indicated at 26, in the middle portion 20 of the shaft 12 for converting the vibration transmitted from the ultrasonic oscillation mechanism 14 into a (longitudinal-torsional) composite vibration composed of a longitudinal vibration in the central axial direction of the shaft 12 and a torsional vibration having the central axis of the shaft 12 as a fulcrum in the vicinity of the distal portion 22. In one embodiment, the vibration conversion mechanism 26 includes a plurality of grooves 28 formed to be wound around the circumferential surface of the middle portion 20 of the shaft 12. It should be appreciated that the vibration conversion mechanism 26 can be located at other portions of the shaft 12 and have other designs.

Figure 5:
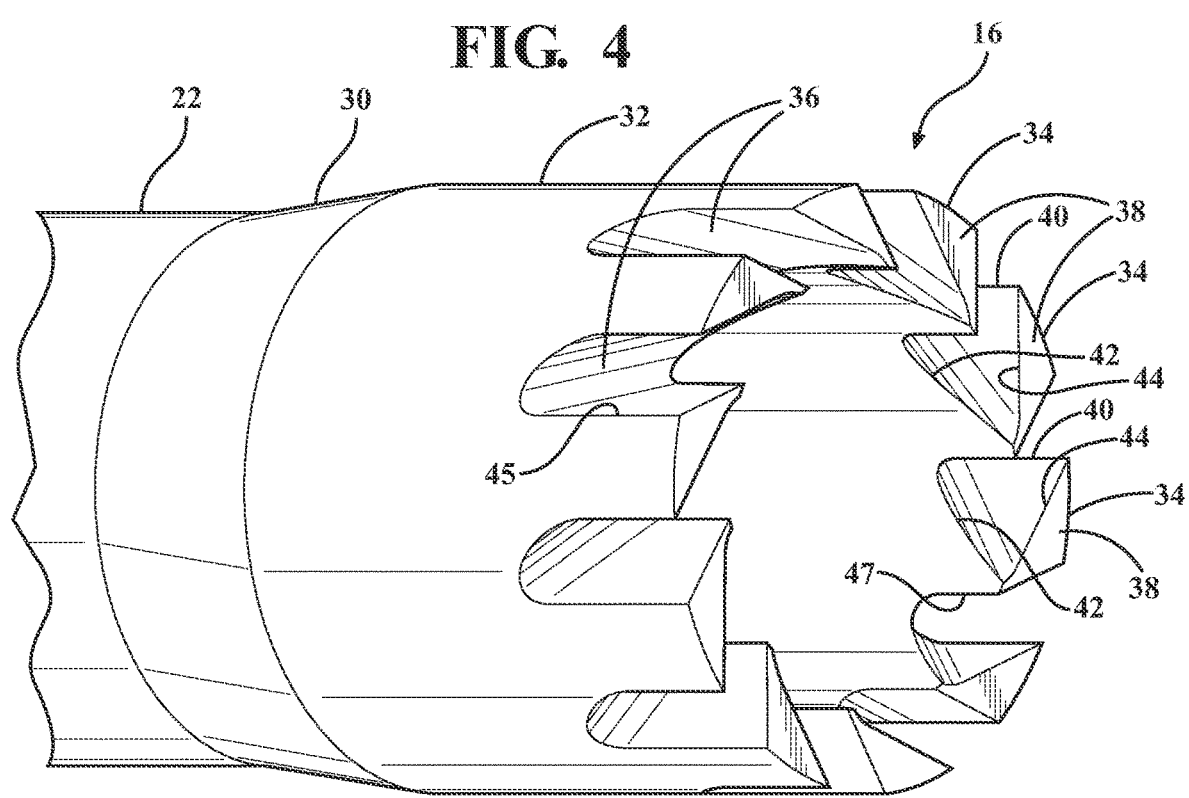
FIG. 5 is an enlarged perspective view of an ultrasonic tip, according to the present invention, for the surgical instrument of FIGS. 1 through 4.
Figure 6:
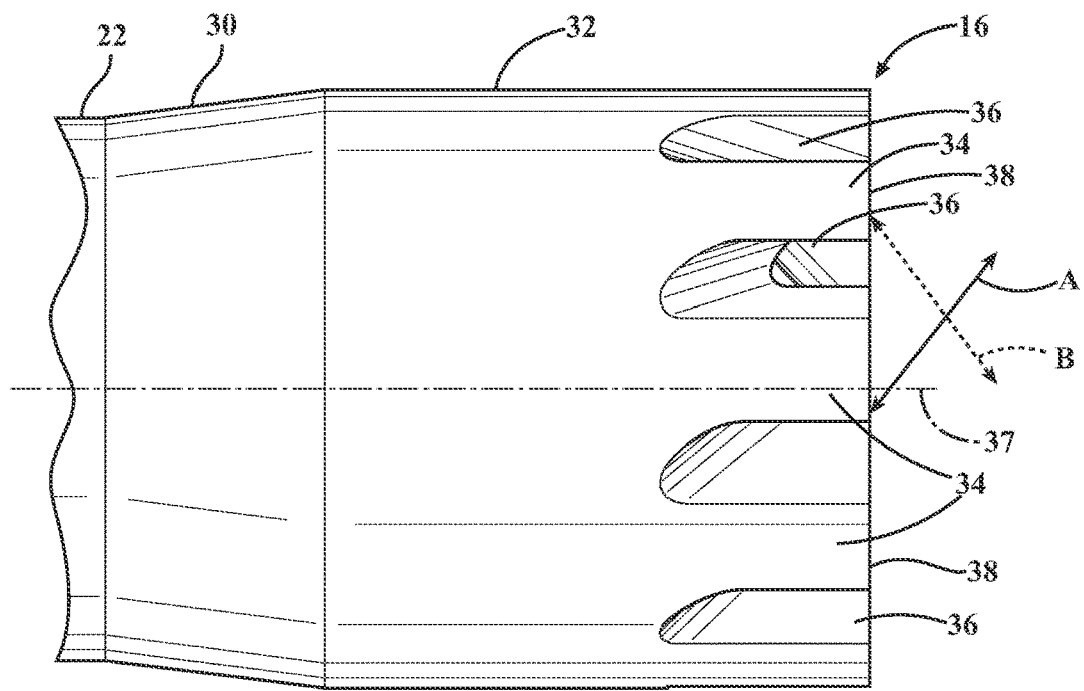
FIG. 6 is an elevational view of the ultrasonic tip of FIG. 5.
Figure 7:
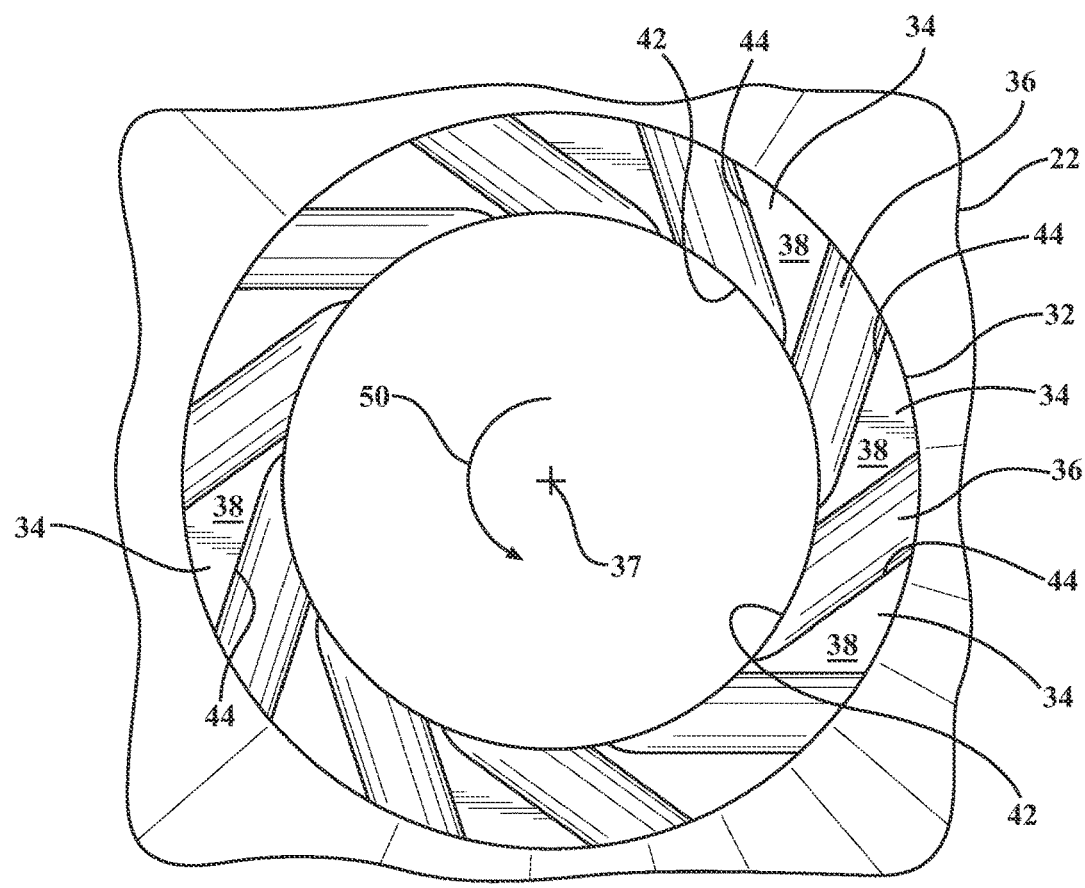
FIG. 7 is a distal end view of the ultrasonic tip of FIG. 5.
Figure 8:
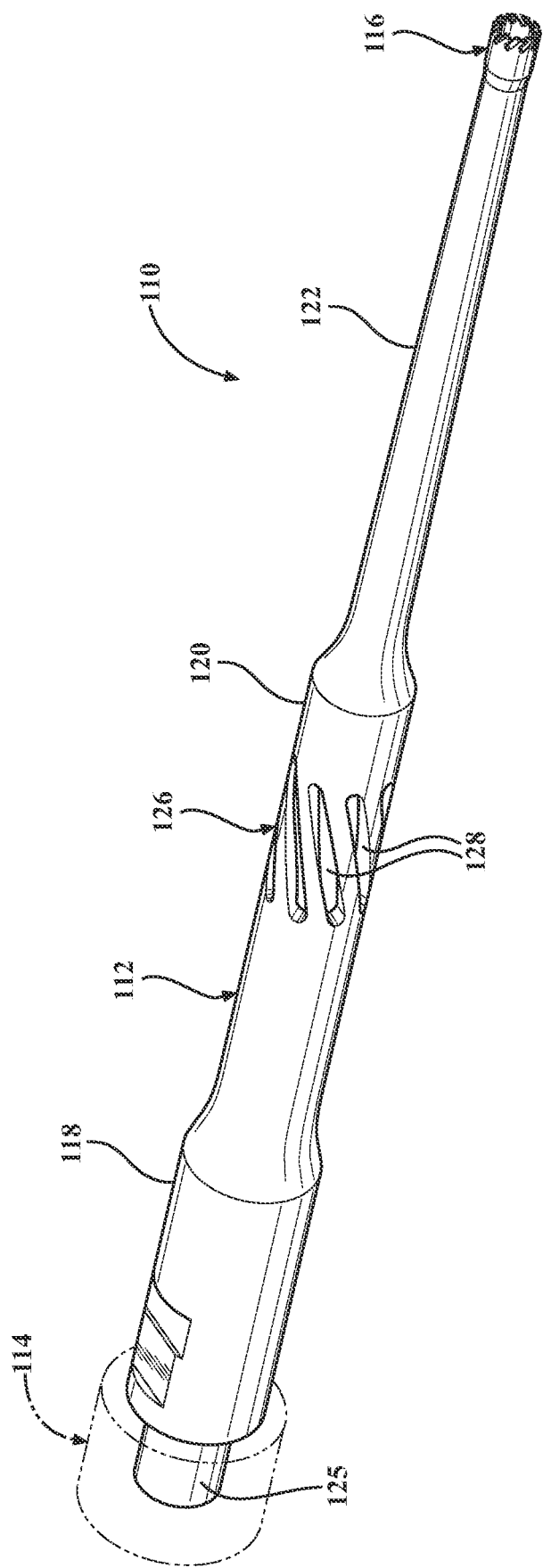
FIG. 8 is a perspective view of another embodiment of a surgical instrument with an ultrasonic tip for fibrous tissue removal, according to the present invention.

Referring to FIGS. 5 through 7, the ultrasonic tip 16 includes a connecting or transition portion 30 and ahead or contacting portion 32 extending axially from the transition portion 30. The transition portion 30 tapers axially and radially outward. The transition portion 30 is hollow and communicates with the passageway 24. The head portion 32 extends axially. The head portion 32 is generally hollow and circular in cross-sectional shape. The head portion 32 is open and communicates with the transition portion 30 and the passageway 24. The head portion 32 has a constant diameter greater than a diameter of the end of the distal portion 22 of the shaft 12.

The ultrasonic tip 16 also includes a plurality of teeth 34 formed at a distal end of the head portion 32. The teeth 34 are formed by cuts or slots 36 extending into and through a wall of the head portion 32 to space the teeth 34 circumferentially about the head portion 32 for a function to be described. The depth of the slots 36 at an outer surface of head portion 32 of the ultrasonic tip 16 is greater than that at an inner surface, resulting in a sloped surface that creates a positive rake angle cutting edge at the inner surface.

In this embodiment, the slots 36 are created along a purely axial direction to extend axially relative to a tip or axial axis 37. The head portion 32 may include any number of teeth 34. One method of forming the distal end geometry is with a rotary cutting disc (not shown). It should be appreciated that the cutting geometry incorporates an axial pattern of slots 36 on the distal end of the ultrasonic tip 16 such that positive rake angles are created between the outer surface and the side surface defining the slots 36. It should also be appreciated that the ultrasonic tip 16 has a distal end geometry that, in combination with an ultrasonic vibrational motion, results in a significant increase in the resection rate of fibrous tissue.

As illustrated in FIGS. 5 through 7, the teeth 34 have a distal end 38, a side cutting edge 40, an inner cutting edge 42, and a distal cutting edge 44. The distal ends 38 of the teeth 34 are generally triangular in shape as opposed to square, resulting in a sharp cutting point at the outer surface and of a single inner cutting edge 42. The distal cutting edge 44 has a positive rake angle. In the embodiment illustrated, the teeth 34 are arranged so that the cutting edges 40, 42, and 44 are all in the same direction and are all in the same axial pattern. In the embodiment illustrated, the surfaces of the distal ends 38 are planar or orientated in the same plane. Also, the sides of the head portion 32 are perpendicular. The slots 36 are defined on the outer surface by the side cutting edge 40 that has a straight axial section and an arcuate section and a relief edge 45. The slots 36 are defined on the inner surface by the inner cutting edge 42 that has an arcuate section that joins with a straight axial relief edge 47. It should be appreciated that a relief surface is defined between the relief edges 45 and 47. It should also be appreciated that, when the distal cutting edge 44 receives torsional motion as indicated by the arrow 50 in FIG. 7, the distal cutting edge 44 meets the tumor with an obtuse angle to create a positive rake angle and cutting action will occur.

The ultrasonic tip 16 may be coated with a suitable coating, for example, such as Titanium Nitride (TiN) or a diamond like coating (DLC). It should be appreciated that the ultrasonic tip 16 achieves the highest resection rate when the distal end 38 of the teeth 34 of the head portion 32 is vibrating in a torsional or a combined longitudinal and torsional motion. It should further be appreciated that the highest resection rate of the surgical instrument 10 occurs when the motion of vibration is perpendicular to the positive rake angle cutting edge of the ultrasonic tip 16.

A control console (not shown) is also part of the system. The control console sources drive signals over a cable (not shown) to the surgical instrument 10. The drive signals are applied to drivers (not shown). At any given instant, the same drive signal is applied to each driver. The application of the drive signals causes the drivers to simultaneously and cyclically expand and contract. A stack of drivers is often between 1 and 5 cm in length. The distance, the amplitude, of movement over a single expansion/contraction cycle of the drivers may be between 1 and 10 microns. The shaft 12 amplifies this movement. Consequently, the distal end of the shaft 12 and, by extension, the head portion 32 of the ultrasonic tip 16 when moving from the fully contracted position to the fully extended position moves typically a maximum of 500 microns and more often 350 microns or less for tips 16 made of titanium alloy. It should be appreciated that the tip 16 may be further designed so that the longitudinal extension/retraction of the tip stem also induces a rotational movement in the head portion 32. It should also be appreciated that, often, when the shaft 12 is in a cyclical movement to cause the cyclic movement of the tip 16, the head portion 32 is considered to be vibrating.

In operation, the ultrasonic tip 16 is ultrasonically excited by the ultrasonic oscillation mechanism 14 and the vibration conversion mechanism 26. The vibrational amplitude at the end of the ultrasonic tip 16 can be in the range of 400 microns peak to peak. There can be suction through the central lumen 24 which aids in coupling the tissue to the ultrasonic tip 16. The distal end 38 of the teeth 34 of the head portion 32 of the ultrasonic tip 16 is brought into contact with the tissue. Ablation of the tissue occurs in part due to methods common to standard ultrasonic aspirators (cavitation, pressure waves, mechanical impact). This occurs when the tissue is in close proximity to the vibrating surfaces. High intensity ultrasonic fields exist within the slots 36 of the vibrating head portion 32 of the ultrasonic tip 16. The optimal motion of the distal end 38 of the teeth 34 is illustrated by arrow A (solid lines) and the motion at the bottom of the teeth 34 is illustrated by arrow B (dotted lines) in FIG. 6. It should be appreciated that a resection mechanism for the ultrasonic tip 16 of the present invention is of mechanical cutting of the fibers in the tissue against the positive rake angled edges of the teeth 34. It should also be appreciated that the ultrasonically oscillating edges of the teeth 34 impact the tissue fibers and impart stresses that result in cutting of the fibers. It should further be appreciated that the edges 40, 42, and 44 of the ultrasonic tip 16 allow for efficient cutting of fibrous tissue and in combination with the common ultrasonic ablation mechanisms and controlled suction result in controlled resection of the tissue.

With the depth of the slots 36 at the outer surface of the ultrasonic tip 16 greater than that at the inner surface, resulting in a sloped surface, the vibrating sharp edge at the inner surface causes slicing of the tissue when it is pulled into the central lumen 24 of the shaft 12. The size of the resected tissue is no greater than an inner diameter of the ultrasonic tip 16, resulting in reduced chance of clogging of the suction path. Due to the oscillatory ultrasonic vibration, the tissue is not wrapped around the ultrasonic tip 16 and controlled resection can occur without unwanted strain on the bulk of the tissue. It should be appreciated that sharp cutting edges 40, 42, and 44 of the teeth 34 ensure clean cuts and minimize dragging of the bulk tissue.

With the depth of the slots 36 at the outer surface of the ultrasonic tip 16 greater than that at the inner surface, resulting in a sloped surface, the air flow through the sides of the tip 16 is reduced when suction is applied. This allows for reduced suction loss and better coupling of the ultrasonic tip 16 with the tissue. The depth of the slots 36 at the outer surface of the ultrasonic tip 16 greater than that at the inner surface, resulting in a slope surface, also controls the depth the tip 16 can intrude into the tissue before slicing of the tissue at the inner edge 42 occurs. It should be appreciated that this feature also results in minimizing unwanted strain on the bulk of the tissue.

Referring to FIGS. 8 through 11, another embodiment, according to the present invention, of the surgical instrument 10 is shown. Like parts of the surgical instrument 10 have like reference numerals increased by one hundred (100). In this embodiment, the surgical instrument 110 includes the shaft 112, extending between a proximal end and a distal end, the ultrasonic oscillation mechanism 114 at the proximal end, and the ultrasonic tip 116, at the distal end for fibrous tissue removal on the patient. The shaft 112 includes the proximal portion 118, the middle portion 120, and the distal portion 122. The shaft 112 also includes the passageway 124 extending axially therethrough from the proximal end to the ultrasonic tip 116. It should be appreciated that the surgical instrument 110 also includes the vibration conversion mechanism 126 in the middle portion 120 of the shaft 112 for converting the vibration transmitted from the ultrasonic oscillation mechanism 114.

Figure 12:
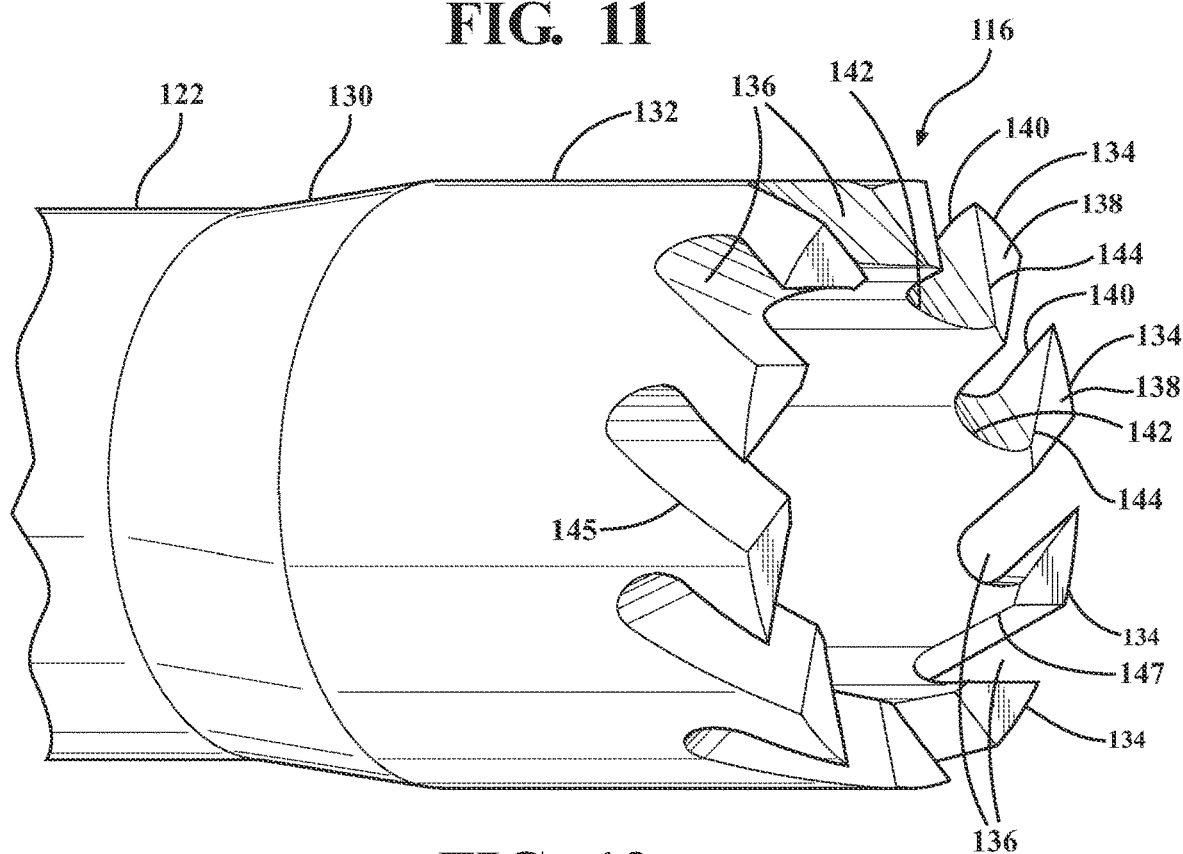
FIG. 12 is an enlarged perspective view of an ultrasonic tip, according to the present invention, for the surgical instrument of FIGS. 8 through 11.
Figure 13:
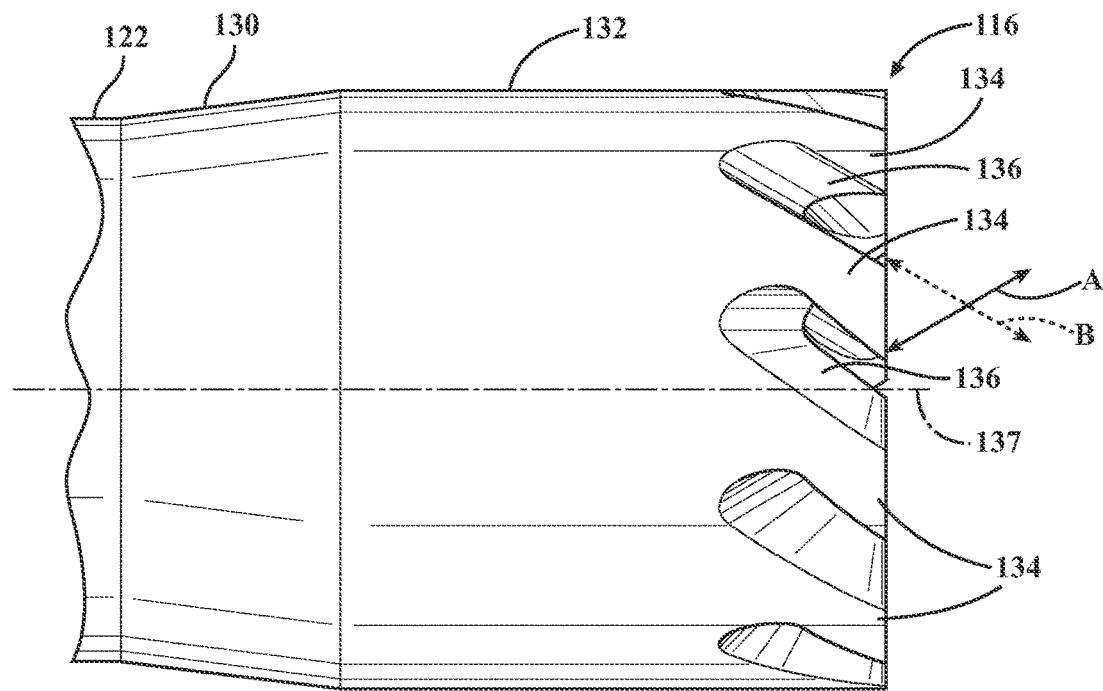
FIG. 13 is an elevational view of the ultrasonic tip of FIG. 12.
Figure 14:
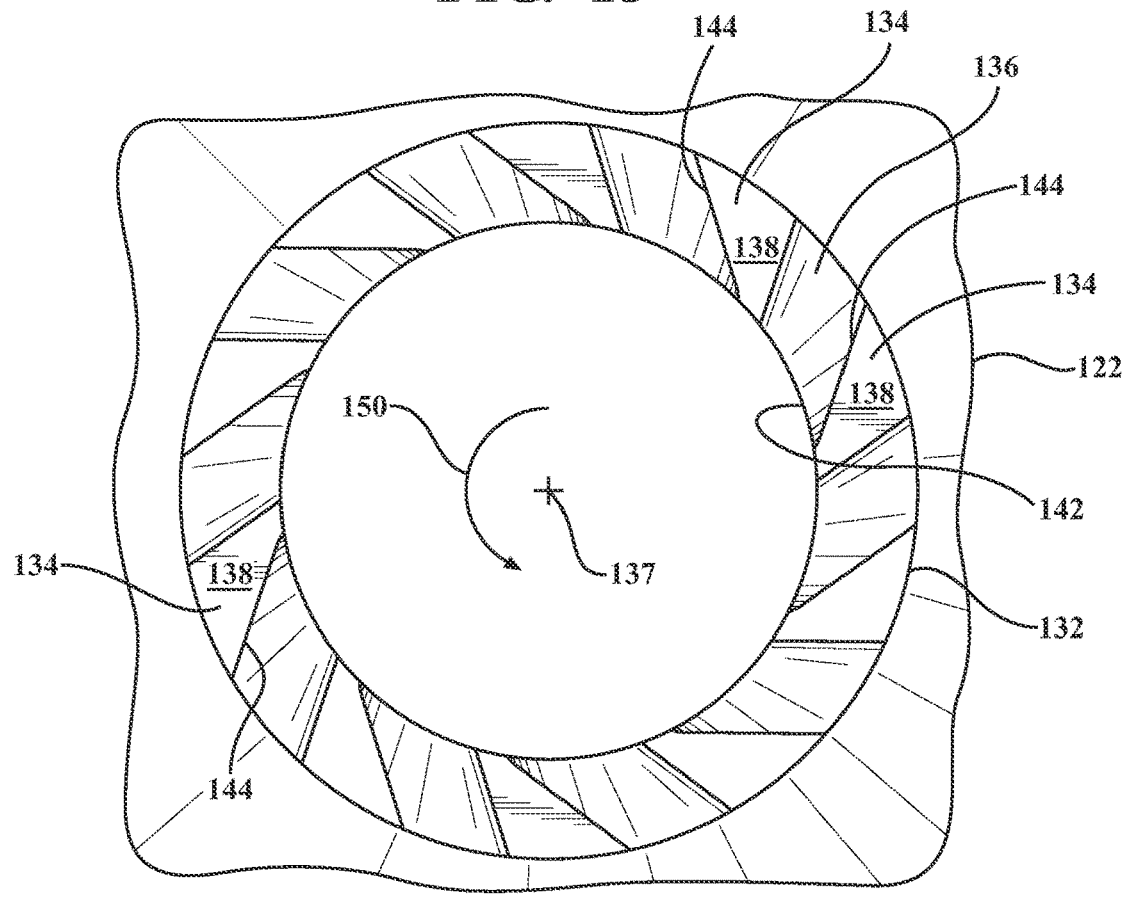
FIG. 14 is a distal end view of the ultrasonic tip of FIG. 12.

Referring to FIGS. 12 through 14, the ultrasonic tip 116 includes the transition portion 130 and the head portion 132 extending axially from the transition portion 130. The ultrasonic tip 116 includes a plurality of teeth 134 formed at the distal end of the head portion 132. The teeth 134 are formed by cuts or slots 136 extending into and through a wall of the head portion 132 to space the teeth 134 circumferentially about the head portion 132. The depth of the slots 136 at an outer surface of the ultrasonic tip 116 is greater than that at the inner surface, resulting in a sloped surface that creates a positive rake angle cutting edge at the inner surface. In this embodiment, the slots 136 are created at an offset angle (in this case the cutting edge at the outer surface is at an acute angle along the outer surface that is parallel to the axis 137). The head portion 132 may include any number of teeth 134. It should be appreciated that the cutting geometry incorporates an axial pattern of slots 136 on the distal end of the ultrasonic tip 116 such that positive rake angles are created between the outer surface and the side surface of the slots 136.

Figure 11:
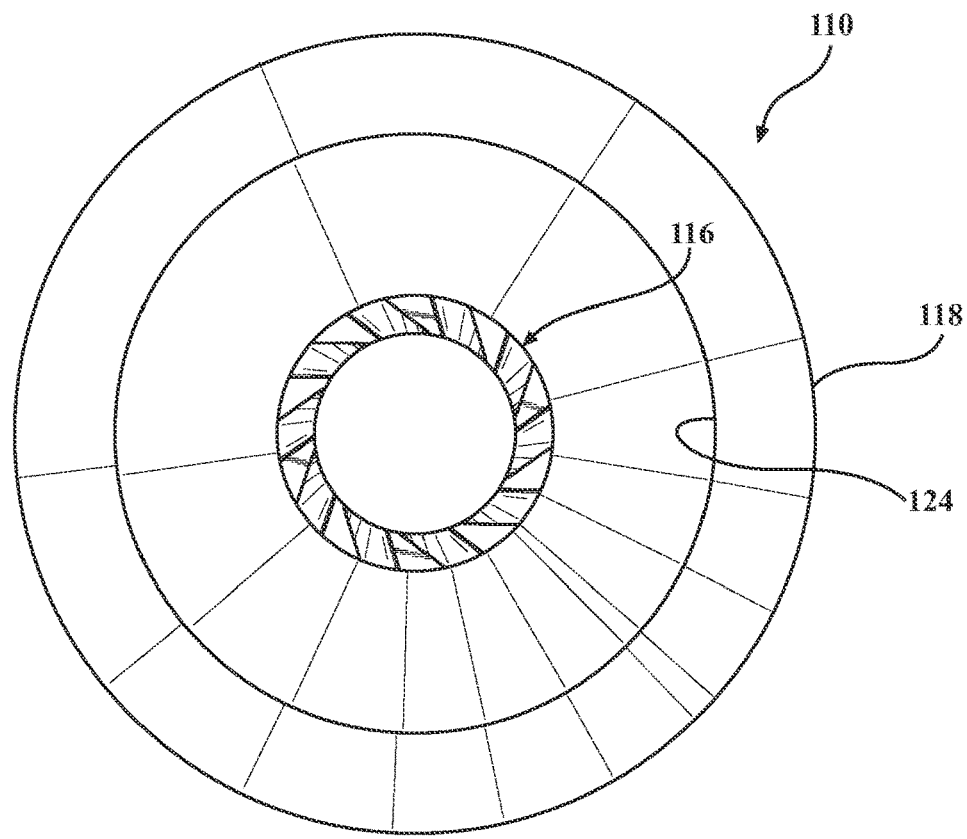
FIG. 11 is a proximal end view of the surgical instrument of FIG. 8.

As illustrated in FIGS. 10 through 12, the teeth 134 have a distal end 138, a side cutting edge 140, an inner cutting edge 142, and a distal cutting edge 144. The distal ends 138 are generally triangular in shape as opposed to square, resulting in a sharp cutting point at the outer diameter and of a single distal cutting inner edge. In this embodiment, the teeth 134 are arranged so that the cutting edges 140, 142, and 144 vary in direction and are not all in the same axial pattern. In the embodiment illustrated, the surfaces of the distal ends 138 are oriented on different planes to each other. In the embodiment illustrated, the sides of the head portion 132 are not perpendicular to ensure efficient cutting and snagging of the underlying tissue. It should also be appreciated that, when the distal cutting edge 144 receives torsional motion as indicated by the arrow 150 in FIG. 14, the distal cutting edge 144 meets the tumor with an obtuse angle to create a positive rake angle, cutting action will occur.

The ultrasonic tip 116 may be coated with a suitable functional coating, for example, such as Titanium Nitride (TiN) or a diamond like coating (DLC). The optimal motion of the distal end 138 of the teeth 134 is illustrated by arrow A (solid lines) and the motion at the bottom of the teeth 134 is illustrated by arrow B (dotted lines) in FIG. 13. It should be appreciated that the ultrasonic tip 116 achieves the highest resection rate when the head portion 132 is vibrating in a torsional or a combined longitudinal and torsional motion. It should further be appreciated that the highest resection rate of the surgical instrument 110 occurs when a component of the motion of vibration is perpendicular to the positive rake angle cutting edge of the ultrasonic tip 116. It should still further be appreciated that the operation of the surgical instrument 110 is similar to the operation of the surgical instrument 10.

In addition, the present invention discloses a method of operating the surgical instrument 10, 110 having the ultrasonic tip 16, 116. The method includes the steps of applying a signal to the surgical instrument 10, 110 and ultrasonically exciting an ultrasonic tip 16, 116 of the surgical instrument 10, 110 and moving the ultrasonic tip 16, 116 into contact with tissue at a surgical site of a patient. The ultrasonic tip 16, 116 has a head portion 32, 132 extending axially along an axial axis 37, 137 to a distal end, the distal end of the ultrasonic tip 16, 116 having a cutting edge 44, 144 with a positive rake angle relative to the axis 37, 137. The method also includes cutting fibers in the tissue against the positive rake angle of the cutting edge 44, 144 of the head portion 32, 132 of the ultrasonic tip 16, 116. It should be appreciated that the method includes other steps.

Accordingly, the surgical instrument 10, 110 of the present invention incorporates an ultrasonic tip 16, 116 having teeth 34, 134 with positive rake angles. When the slots 36, 136 are perpendicular to the direction of vibration of the ultrasonic tip 16, 116 higher resection rates can be obtained. When the surfaces of the distal end 38, 138 of the teeth 34, 134 of the ultrasonic tip 16, 116 are orientated on different planes to each other, a reduction in the contact area and pressure against the tissue could be achieved. This could result in a reduction in the frictional heating between the tip surface and the tissue. When the sides of the head portion 32, 132 of the ultrasonic tip 16, 116 are not perpendicular, then a reduction in the contact area and pressure against the tissue could be achieved. This could result in a reduction in the frictional heating between the tip surface and the tissue.

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

What is claimed is:

1. A surgical instrument configured to be coupled to an ultrasonic oscillation mechanism for resection of tissue under suction, said surgical instrument comprising:
   a shaft defining a passageway and comprising a vibration conversion mechanism configured to convert vibration transmitted from the ultrasonic oscillation mechanism to a composite motion relative to a longitudinal axis of the shaft; and
   a tip extending from said shaft and comprising an inner surface, the inner surface defining a lumen in communication with said passageway of said shaft, an outer surface opposite said inner surface of the lumen, and teeth formed by slots extending from said inner surface of the lumen to said outer surface so that said teeth are circumferentially arranged about said tip, wherein said composite motion of said shaft is configured to move said tip in a combined longitudinal and torsional vibration in a first direction, and in a second direction opposite the first direction,
   wherein each of said teeth comprises a planar distal end, a distal cutting edge extending between said inner surface of the lumen and said outer surface at said planar distal end, and a side cutting edge defined between said outer surface and a side surface defining one of said slots, wherein said distal cutting edge and said side cutting edge are configured to slice the tissue with the tip moving in the first direction and pull the tissue with the tip moving in the second direction.

2. The surgical instrument of claim 1, wherein said slots are at an offset angle relative to an axial direction parallel to the longitudinal axis such that a triangular portion of said teeth defined between said distal cutting edge, said side cutting edge, and an arcuate portion of said slots is configured to pull the tissue with the tip moving in the second direction.

3. The surgical instrument of claim 2, wherein said planar distal end tapers outwardly from said inner surface to said outer surface such that said triangular portion and said planar distal end are configured to wedge said teeth into the tissue with the tip moving in the first direction.

4. The surgical instrument of claim 1, wherein each of said teeth further comprises a relief edge defined between said outer surface and another side surface defining another one of said slots, wherein said relief edge is configured to slice the tissue with the tip moving in the second direction.

5. The surgical instrument of claim 1, wherein said distal cutting edge and said side cutting edge are configured to meet the tissue with a positive rake angle with the tip moving in the first direction.

6. The surgical instrument of claim 1, wherein said slots are defined by a sloped surface forming, with said inner surface of the lumen, an inner cutting edge configured to meet the tissue with a positive rake angle with the tip moving in the first direction.

7. The surgical instrument of claim 1, wherein said tip further comprises a sharp cutting point at an intersection between said distal cutting edge; and said side cutting edge at said planar distal end.

8. A surgical instrument configured to be coupled to an ultrasonic oscillation mechanism for resection of tissue under suction, said surgical instrument comprising:
   a shaft defining a passageway and comprising a vibration conversion mechanism configured to convert vibration transmitted from the ultrasonic oscillation mechanism to a composite motion including longitudinal vibration and torsional vibration; and
   a tip extending from said shaft and comprising an inner surface, the inner surface defining a lumen in communication with said passageway of said shaft and defining a suction path, an outer surface opposite said inner surface of the lumen, and teeth formed by slots extending from said inner surface of the lumen to said outer surface that said teeth are circumferentially arranged about said tip,
   wherein each of said teeth comprises a planar distal end, a distal cutting edge extending between said inner surface of the lumen and said outer surface at said planar distal end, and a side cutting edge defined between said outer surface and a side surface defining one of said slots, wherein a depth of said slots at said outer surface is greater than at said inner surface of the lumen to provide a sloped surface for maintaining coupling of said tip with the tissue with suction during resection of the tissue with said distal cutting edge and said side cutting edge.

9. The surgical instrument of claim 8, wherein said planar distal end tapers outwardly from said inner surface to said outer surface such that said teeth are configured to wedge into the tissue for slicing the tissue to be drawn through said suction path.

10. The surgical instrument of claim 8, wherein said sloped surface forms with said inner surface of the lumen an inner cutting edge configured to slice the tissue in the longitudinal vibration to a size no greater than said lumen to prevent clogging of said suction path.

11. The surgical instrument of claim 8, wherein said tip further comprises a sharp cutting point at an intersection between said distal cutting edge and; said side cutting edge at said planar distal end.

12. A surgical instrument configured to be coupled to an ultrasonic oscillation mechanism for resection of tissue under suction, said surgical instrument comprising:
   a shaft defining a passageway and comprising a vibration conversion mechanism configured to convert vibration transmitted from the ultrasonic oscillation mechanism to a composite motion including longitudinal vibration and torsional vibration; and
   a tip extending from said shaft and comprising an inner surface, said inner surface defining a lumen in communication with said passageway of said shaft, an outer surface opposite said inner surface of the lumen, and teeth formed by slots extending from said inner surface of the lumen to said outer surface so that said teeth are circumferentially arranged about said tip,
   wherein each of said teeth comprises a planar distal end, an outer edge defined between said outer surface and said planar distal end, a distal cutting edge extending between said inner surface of said lumen and said outer surface at said planar distal end, and a side cutting edge defined between said outer surface and a side surface of one of said slots, and wherein an intersection of said outer edge, said distal cutting edge, and said side cutting edge defines a sharp cutting point at said planar distal end.

13. The surgical instrument of claim 12, wherein each of said teeth comprises a triangular portion defined between said distal cutting edge, said side cutting edge, and an arcuate portion of said slots.

14. The surgical instrument of claim 13, wherein said planar distal end tapers outwardly from said inner surface to said outer surface such that said triangular portion and said planar distal end are configured to wedge said teeth into the tissue during the composite motion.

15. The surgical instrument of claim 13, wherein said planar distal end is also triangular in shape.

16. The surgical instrument of claim 12, wherein an inner edge defined between said planar distal end and said inner surface of the lumen is shorter in length than an outer edge defined between said planar distal end and said outer surface.

17. The surgical instrument of claim 12, wherein each of said teeth further comprises a relief edge defined between said outer surface and another side surface defining another one of said slots.

18. The surgical instrument of claim 12, wherein said distal cutting edge and said side cutting edge are configured to meet the tissue with a positive rake angle in a first direction of the torsional vibration.

19. The surgical instrument of claim 12, wherein said slots are defined by a sloped surface forming, with said inner surface of the lumen, an inner cutting edge configured to meet the tissue with a positive rake angle in the longitudinal vibration.

20. The surgical instrument of claim 12, wherein said tip further comprises a transition portion extending from said shaft and tapering radially outwardly, and a head portion extending from said transition portion and having a constant outer diameter greater than a diameter of a distal portion of said shaft, wherein said shaft, said transition portion of said tip, and said head portion of said tip are integral, unitary, and one-piece.

21. The surgical instrument of claim 12, wherein said slots extend axially at an offset angle such that said side cutting edges are at an acute angle relative to an axial direction parallel to a longitudinal axis of the shaft.

* * * * *